United States Patent [19]

Durant et al.

[11] 4,317,829

[45] Mar. 2, 1982

[54] TRIAZOLE-SUBSTITUTED ETHYLENE DERIVATIVES

[75] Inventors: Graham J. Durant, Welwyn Garden City; John C. Emmett, Codicote; Charon R. Ganellin, Welwyn Garden City; Hunter D. Prain, Welwyn, all of England

[73] Assignee: Smith Kline & French Laboratories Limited, Welwyn Garden City, England

[21] Appl. No.: 117,901

[22] Filed: Feb. 4, 1980

Related U.S. Application Data

[60] Division of Ser. No. 930,102, Aug. 1, 1978, Pat. No. 4,220,652, which is a division of Ser. No. 797,160, May 16, 1977, Pat. No. 4,124,717, which is a division of Ser. No. 629,174, Nov. 5, 1975, Pat. No. 4,046,907, which is a continuation-in-part of Ser. No. 468,617, May 9, 1974, Pat. No. 3,953,460.

[30] Foreign Application Priority Data

May 17, 1973 [GB] United Kingdom ............... 23568/73

[51] Int. Cl.$^3$ .................... A61K 31/41; C07D 249/04; C07D 249/08; C07D 249/12
[52] U.S. Cl. .................................. 424/269; 542/416; 548/255; 548/262; 548/263; 548/264; 548/265; 548/266; 548/269
[58] Field of Search ................ 542/416, 414; 548/255, 548/262, 263, 264, 265, 266, 269; 424/269

[56] References Cited

U.S. PATENT DOCUMENTS 3,404,159  10/1968  Strobel et al. ...................... 548/262

*Primary Examiner*—Alton D. Rollins
*Attorney, Agent, or Firm*—Joan S. Keps; Richard D. Foggio; Alan D. Lourie

[57] ABSTRACT

The compounds are ethylene derivatives which are inhibitors of histamine activity, in particular, inhibitors of H-2 histamine receptors. A compound of this invention is 1-nitro-2-methylamino-2-[2-((4-methyl-5-imidazolyl)methylthio)ethylamino]ethylene.

6 Claims, No Drawings

TRIAZOLE-SUBSTITUTED ETHYLENE DERIVATIVES

This is a division of application Ser. No. 930,102 filed Aug. 1, 1978, now U.S. Pat. No. 4,220,652, which is a division of application Ser. No. 797,160 filed May 16, 1977, now U.S. Pat. No. 4,124,717, which is a division of application Ser. No. 629,174 filed Nov. 5, 1975, now U.S. Pat. No. 4,046,907, which is a continuation-in-part of application Ser. No. 468,617 filed May 9, 1974, now U.S. Pat. No. 3,953,460.

This invention relates to ethylene derivatives, in particular to pharmacologically active 1,1-diaminoethylene derivatives. These compounds are inhibitors of H-2 histamine receptors. In addition, this invention relates to pharmaceutical compositions comprising these compounds and to methods of inhibiting H-2 histamine receptors with these compounds. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has been described by Black et. al (Nature 1972, 236, 385) which are distinguished by the fact that they act at histamine receptors other than the H-1 receptor and these other receptors have been designated as H-2 receptors. This latter group of substances, to certain of which the present invention relates, are thus of utility in inhibiting certain actions of histamine which are not inhibited by the above-mentioned "antihistamines", that is they are H-2 histamine receptor inhibitors. Inhibitors of H-2 histamine receptors are useful, for example, as inhibitors of gastric acid secretion. The substances of this invention may also be of utility as inhibitors of certain actions of gastrin. In the treatment of certain conditions, for example inflammation, and in inhibiting the actions of histamine on blood pressure, combination of H-1 and H-2 receptor inhibitors is useful.

The 1,1-diaminoethylene derivatives withwhich the present invention is concerned may be represented by the following general formula:

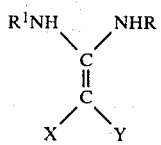

FORMULA I wherein X and Y, which may be the same or different, are hydrogen, nitro, cyano or $SO_2Ar$ but are not both hydrogen; $R^1$ is Het—$(CH_2)_mZ(CH_2)_n$; R is hydrogen, lower alkyl such as methyl or, being the same as or different from R', Het—$(CH_2)_mZ(CH_2)_n$; Z is sulphur or methylene; m is 0, 1 or 2 and n is 2 or 3 provided that the sum of m and n is 3 or 4; Het is a nitrogen containing 5 membered heterocylic ring such as imidazole, oxazole, isoxazole, triazole, thiazole, isothiazole or thiadiazole which ring is optionally substituted by lower alkyl, hydroxyl, halogen or amino; and Ar is an aryl group such as phenyl optionally substituted by halogen or methyl, or a pharmaceutically acceptable acid addition salt thereof.

It will be appreciated, in the case where R is Het—$(CH_2)_m$—$Z(CH_2)_n$, that Het, m, n and Z need not have the identical significance as in $R^1$.

Throughout the present specification by the term "lower alkyl" we mean an alkyl group containing from 1 to 4 carbon atoms.

It will be understood that the structure illustrated in Formula I and in Formula I (a) below, is only one of several representations and that other tautomeric forms as shown in Formulae II and III and the other geometrical isomers shown in Formula IV are also covered by the present invention. In Formulae II to IV and I (a) $R^1$ represents Het—$(CH_2)_m$—$Z(CH_2)_n$.

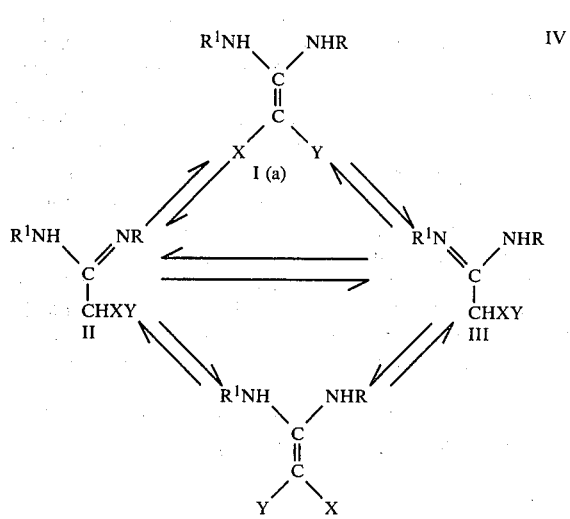

In a preferred group of compounds of Formula I, R is methyl or Het—$CH_2SCH_2CH_2$, Z is sulphur, m is 1 and n is 2. Most suitably Het is imidazole, thiazole or isothiazole and is optionally substituted by methyl or halogen.

It is also preferred that X should be nitro and Y should be hydrogen.

Particularly useful compounds are:

1-nitro-2-methylamino-2-[2-(4-methyl-5-imidazolylmethylthio)ethylamino]ethylene, 1-nitro-2,2-bis-[2-(4-methyl-5-imidazolylmethylthio)ethylamino]ethylene, 1-nitro-2-methylamino-2-[(2-thiazolylmethylthio)ethylamino]ethylene and 1-nitro-2,2,-bis-[2-(2-thiazolylmethylthio)ethylamino]ethylene.

A general method for the preparation of the compounds of the present invention is shown in the following Scheme 1:

SCHEME 1

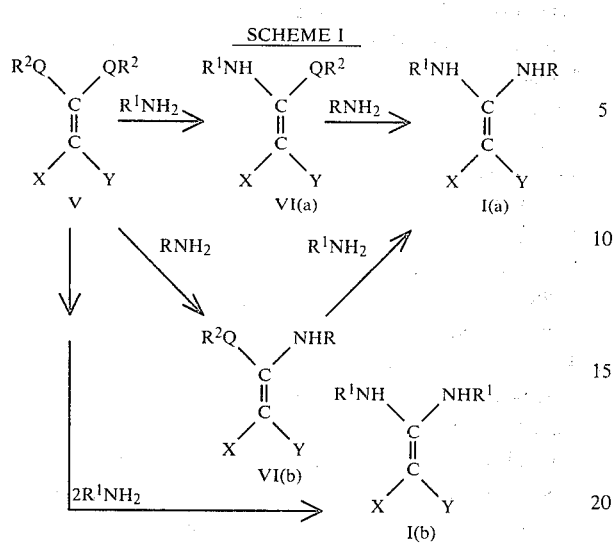

The starting material is a compound of Formula V wherein Q is sulphur or oxygen, preferably sulphur, and $R^2$ is lower alkyl such as methyl, or aralkyl, such as benzyl, but is preferably methyl. This may be reacted with one equivalent of $R^1NH_2$ or of $RNH_2$, $R^1$ and R have the same significance as in Formula I, to give respectively the compounds of Formulae VI(a) or VI(b) and then reacted with $RNH_2$ or $R^1NH_2$ respectively to give the compound of Formula I(a). In the case wherein R is the same as $R^1$ the reaction may be carried out in a single step by reacting the compound of Formula V with two equivalents of $R^1NH_2$ to give the product of Formula I(b). The reactions described in Scheme 1 may be carried out in a suitable solvent, or, particularly when R is the same as $R^1$ in the absence of a solvent at a moderately elevated temperature, for example at from 90°–150° C.

The intermediate of Formula V wherein Q is sulphur (see Formula V(a) in the following Scheme (2):

SCHEME 2

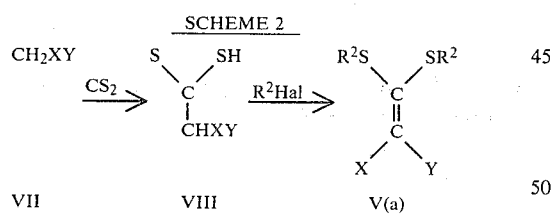

may be formed from the substituted methane of Formula VII by treatment of the latter with a strong base such as sodium hydride or sodium hydroxide and reaction with carbon disulphide to give the compound of Formula VIII. Treatment of this substance with an alkyl or aralkyl halide of Formula $R^2$ Hal gives the required compound of Formula V(a).

An alternative method for the preparation of the compounds of Formula I(a) is shown in Scheme 3.

SCHEME 3

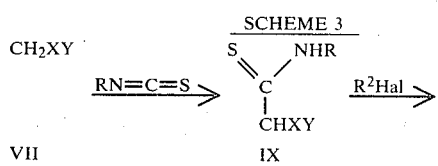

-continued
SCHEME 3

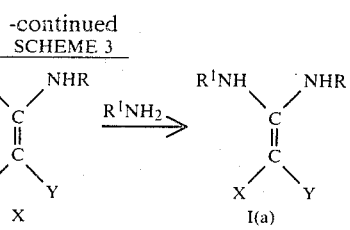

The substituted methane of Formula VII, after treatment with a strong base such as sodium hydride or sodium hydroxide, may be reacted with an isothiocyanate ester of Formula $RN=C=S$ wherein R is lower alkyl to give the compound of Formula IX and reaction of this with the alkyl or aralkyl halide of Formula $R^2$ Hal results in the compound of Formula X wherein R is lower alkyl. Further reaction of the compound of Formula X with an amine of Formula $R^1NH_2$ yields the required compound of Formula I(a).

A further method which may be used in the preparation of compounds wherein R is hydrogen, X is $SO_2Ar$ and Y is hydrogen (Formula I (c)) is shown in Scheme 4:

SCHEME 4

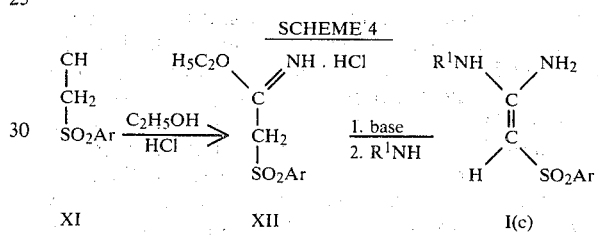

The arylsulphonylacetonitrile of Formula XI wherein Ar has the same significance as in Formula I is reacted under anhydrous conditions with ethanol and hydrogen chloride to give the iminoether of Formula XII. Treatment of this with a base and subsequent reaction with an amine of Formula $R^1NH_2$ gives the required product of Formula I(c).

It will be appreciated that the final stage of the reactions shown in Scheme 1, 3 and 4 may all be expressed by the following reaction:

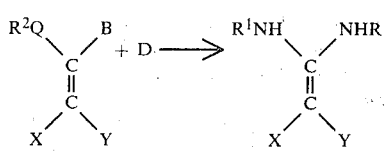

wherein B is RNH or $R^1NH$; D is $R^1NH_2$ or $RNH_2$; X, Y, R and $R^1$ have the same significance as in Formula I(a) and Q and $R^2$ have the same significance as in Formula V, provided that, when B is RNH, D must be $R^1NH_2$.

As stated above, the compounds represented by Formula I have been found to have pharmacological activity in the animal body as antagonists to certain actions of histamine which are not blocked by "antihistamines" such as mepyramine. For example they have been found to inhibit selectively the histamine-stimulated secretion of gastric acid from the perfused stomachs of rats anesthetised with urethane at doses of from 0.5 to 256 micromoles per kilogram intravenously. Similarly, the action of these compounds is demonstrated by their antagonism to the effects of histamine on other tissues which, according to the above-mentioned paper of Black et. al., are H-2 receptors. Examples of such tissues are perfused isolated guinea-pig atrium and isolated rat uterus. The compounds of the invention have also been found to inhibit the secretion of gastric acid stimulated by pentagastrin or by food.

The level of activity found for the compounds of the present invention is illustrated by the effective dose range in the anaesthetised rat, as mentioned above of from 0.5 to 256 micromoles per kilogram, intravenously. Many of the compounds of the present invention produce a 50% inhibition in this test at a dose of from 1 to 10 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol.

Pharmaceutical compositions comprising a pharmaceutical carrier and a compound of Formula I or a pharmaceutically acceptable acid addition salt thereof and methods of inhibiting H-2 histamine receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg to about 250 mg, most preferably from about 100 mg to about 200 mg.

The active ingredient will preferably be administered in equal doses one to three times per day. The daily dosage regimen will preferably be from about 150 mg to about 750 mg, most preferably from about 300 mg to about 600 mg.

Other pharmacologically active compounds may in certain cases be included in the composition. Advantageously the composition will be made up in a dosage unit form appropriate to the desired mode of administration, for example as a tablet, capsule or injectable solution. The invention is illustrated but in no way limited by the following Examples:

EXAMPLE 1

1,1-Dicyano-2-methylamino-2-[2-((4-methyl-5-imidazolyl)-methylthio)ethylamino]ethylene Method (a)

(i) Sodium hydride (50% oil dispersion, 9.6 g) was added portionwise to a solution of malononitrile (13.21 g) in dry dimethylformamide (150 ml). The mixture was stirred at 0° for 10 minutes and then to it was added dropwise a solution of methyl isothiocyanate (14.62 g) in dimethylformamide, maintaining the reaction temperature below 40°. The dark red solution was stirred for 45 minutes and a solution of methyl iodide (28.4 g) in dimethylformamide (25 ml) was then added. The reaction mixture was stirred vigorously for 20 minutes and then poured on to crushed ice (500 ml). The crude product (26 g, m.p. 115°) was filtered off and taken up in hot ethanol ether (3:1, 600 ml). Filtration and cooling furnished 1,1-dicyano-2-methylthio-2-methylamino ethylene m.p. 119°–120°. Further recrystallisation from water gave a sample of m.p. 120°–121°.

(Found: C, 46.7; H, 4.6; N, 27.1; S, 20.8; $C_6H_7N_3S$ requires: C, 47.0; H, 4.4; N, 27.4; S, 20.9)

(ii) To a stirred suspension of 4-methyl-5-[2-aminoethyl)thiomethyl]imidazole (1.71 g) in dry acetonitrile (30 ml) was added 1,1-dicyano-2-methylthio-2-methylamino ethylene (1.53 g). The mixture was stirred at room temperature for one hour and the crude product (1.36 g) was collected. Recrystallisation from boiling water furnished 1,1-dicyano-2-methylamino-2-[2-((4-methyl-5-imidazolyl)methylthio)ethylamino]ethylene, m.p. 133°–135°.

(Found: C, 52.4; H, 5.8; N, 30.5; S, 11.6; $C_{12}H_{16}N_6S$ requires: C, 52.2; H, 5.8; N, 30.4; S, 11.6).

Method (b)

A mixture of 1,1-dicyano-2-ethoxy-2-methylaminoethylene (2.27 g) and 4-methyl-5-[(2-aminoethyl)thiomethyl]imidazole (2.57 g) in acetonitrile (25 ml) was stirred at room temperature for 23 hours. The reaction mixture was then evaporated to dryness and the residual oil chromatographed on silica gel using acetone as eluent to give, after removal of the solvent, 1,1-dicyano-2-methylamino-2-[2-((4-methyl-5-imidazolyl)methylthio)ethylamino]ethylene, m.p. 131°–133°.

EXAMPLE 2

1-Nitro-2-methylamino-2-[2-(4-methyl-5-imidazolyl)-methylthio)ethylamino]ethylene (i) A solution of 4-methyl-5-[(2-aminoethyl)thiomethyl]imidazole (1.71 g) in t-butanol (30 ml) was added slowly to a solution of 1-nitro-2,2-bis-methylthioethylene (1.66 g) in acetonitrile (20 ml) at room temperature. The solution was heated under reflux for 3 hours, evaporated to dryness and chromatographed on a column of silica gel with elution by anhydrous ether (250 ml) followed by acetone (500 ml). The acetone eluate was concentrated to low bulk to give 1-nitro-2-methylthio-2[2-(4-methyl-5-imidazolyl)methylthio)ethylamino]ethylene (1.58 g), m.p. 151°–153°. A sample recrystallised from acetonitrile had m.p. 152°–153°.

(Found: C, 41.4; H, 5.3; N, 19.4; S, 21.8; $C_{10}H_{16}N_4O_2S_2$ requires: C, 41.7; H, 5.6; N, 19.4; S, 22.2)

(ii) A mixture of 1-nitro-2-methylthio-2-[2-(4-methyl-5-imidazolyl)methylthio)ethylamino]ethylene (0.67 g) and 33% ethanolic methylamine (4 ml) was heated in a sealed tube at 70°–80° for one hour. Concentration, followed by purification of the product by chromatography on a column of silica gel with acetone as eluant and recrystallisation from acetonitrile furnished 1-nitro-2-methylamino-2-[2-((4-methyl-5-imidazolyl)methylthio)ethylamino]ethylene (0.39 g), m.p. 141°–3°. Further recrystallisation from isopropanol furnished a sample m.p. 148°–151°.

(Found: C, 44.5; H, 6.6; N, 25.9; S, 11.4; $C_{10}H_{17}N_5O_2S$ requires: C, 44.3; H, 6.3; N, 25.8; S, 11.8)

EXAMPLE 3

1-Nitro-2,2-bis[2-(4-methyl-5-imidazolylmethylthio)ethylamino]ethylene

A mixture of 4-methyl-5-[(2-aminoethyl)thiomethyl]imidazole (6.82 g) and 1-nitro-2,2-bis-methylthio ethylene (3.30 g) was heated at 140° for 2 hours. The product was chromatographed on a column of silica gel with elution by ethanolethylacetate (1:4) to separate 1-nitro-2-methylthio-2-[2-(4-methyl-5-imidazolyl)methylthio)ethylamino]ethylene (0.56 g, m.p. 150°–151° from ethanol-ether) and further elution by ethanol-ethyl acetate (3:2) to separate the title compound (6.5 g, m.p. 152°–153° from ethanol-ether)

(Found: C, 46.5; H, 6.1; N, 23.6; S, 15.5%: $C_{16}H_{25}N_7O_2S_2$ requires: C, 46.7; H, 6.1; N, 23.8; S, 15.5%)

EXAMPLE 4

1-Benzenesulphonyl-2-amino-[2-(4-methyl-5-imidazolyl)methylthio)ethylamino]ethylene dihydrochloride Phenylsulphonyl acetonitrile (14.5 g) was suspended in anhydrous ether (100 ml) containing absolute ethanol (3.0 g) and into the stirred suspension was passed hydrogen chloride with stirring to a weight gain of 6.0 grams. Stirring was continued in the cold for 24 hours and the reaction mixture was then set aside in the cold for 3 days. The crystalline iminoether hydrochloride (13.4 g) m.p. 148°–9° was collected. A solution of this hydrochloride (6.82 g) in aqueous potassium carbonate was extracted with ether and the ether extracts dried and concentrated which gave the imino ether as the free base. This was dissolved in acetonitrile (50 ml) containing 4-methyl-5-[(2-aminoethyl)thiomethyl]imidazole (5.1 g) and the solution was left at room temperature for 24 hours, heated at 50° for 5 hours and finally heated at reflux for 1 hour. The product was chromatographed on a column of neutral alumina with elution by ethanol-ethyl acetate (3:2). The eluate was converted into a picrate which was recrystallised from nitromethane to afford the title compound as the dipicrate m.p. 175°–177°.

(Found: C, 39.8; H, 3.2; N, 17.5; S, 7.9%; $C_{15}H_{20}N_4O_2S_22C_6H_3N_3O_7$ requires: C, 40.0; H, 3.2; N, 17.3; S, 7.9%)

The dipicrate (0.5 g) was dissolved in aqueous methanol (1:1, 50 ml) and ion-exchanged to chloride on a column (IRA 401) in the Cl⁻ form. The eluate was lyophilised and dissolved in water to provide an aqueous solution of the title compound dihydrochloride (Found: Cl, 16.4% $C_{15}H_{20}N_4O_2S_22HCl$ requires: Cl, 16.7%)

EXAMPLE 5

2-Amino-1,1-dicyano-2-[2-(4-methyl-5-imidazolyl)methylthio)ethylamino]ethylene

A solution of 4-methyl-5-[(2-aminoethyl)thiomethyl]imidazole (4.1 g) and 2-amino-1,1-dicyano-2-methylthioethylene (2.3 g) in ethanol was heated under reflux for 2.5 hours. Concentration followed by chromatographic purification on a column of silica gel with ethyl acetate as eluent afforded the title compound (1.32 g), m.p. 187°–188°.

(Found: C, 50.2; H, 5.4; N, 31.6; S, 11.7% $C_{11}H_{14}N_4S_6$ requires: C, 50.4; H, 5.4; N, 32.0; S, 11.2%)

EXAMPLE 6

1-Nitro-2-ethylamino-2-[2-(4-methyl-5-imidazolyl)methylthio]ethylamino-ethylene Reaction of 1-nitro-2-methylthio-2[2-((4-methyl-5-imidazolyl)methylthio)ethylamino]ethylene with ethylamine according to the process of Example 2(ii) yielded the title compound, m.p. 171°–172°.

(Found: C, 46.2; H, 6.7; N, 24.3; S, 11.0% $C_{11}H_{19}H_5O_2S$ requires: C, 46.3; H, 6.7; N, 24.5; S, 11.2%).

EXAMPLE 7

1-Cyano-2-methylamino-2-[2-(4-methyl-5-imidazolyl methylthio) ethylamino]ethylene 4-Methyl-5-[(2-aminoethyl)thiomethyl]imidazole (3.5 g) was added to a solution of 1-cyano-2-ethoxy-2-methylaminoethylene in pyridine (3.1 g) and the solution was stirred for 5 hours at 100°. The product was chromatographed on a column of neutral alumina with elution by chloroform/ethyl acetate (1:1) to give the title compound as a glass.

The NMR spectrum in $CdCl_3$, recorded at 60 mHz showed the following resonances:

| | |
|---|---|
| imidazole-2-H: singlet at $\delta 7.46$ | integral 1.2 protons: calculated, 1.0 protons |
| imidazole-$CH_2$: singlet at $\delta 3.71$ | integral 2.0 protons: calculated 2.0 protons |
| S—$CH_2$—$CH_2$—N: multiplet at 187–215 $H_z$ vinylic-H: singlet at $\delta 2.85$ | integral 2.4 protons |
| S—$CH_2$—$CH_2$—N: multiplet 145–183 $H_z$ —$NHCH_3$: singlet at $\delta 2.77$ | integral 6.07 protons calculated 6.0 protons |
| $CH_3$—imidazole: singlet at $\delta 2.2$ | The integral was used as the internal standard equal to 3.0 protons. |

Mass Spectrum : m/e : 251 (Molecular weight : 251).

EXAMPLE 8

1-Nitro-2-methylamino-2-[4-(4-imidazolyl)-butylamino]ethylene (i) A solution of 4-(4-aminobutyl)imidazole (from the dihydrobromide (3.6 g)) and 1-nitro-2,2-bis-methylthioethylene (2.0 g) in acetonitrile (50 ml) was set aside at room temperature for 3 days. The product was chromatographed on a column of silica gel to give 1-nitro-2-methylthio-2-[4-(4-imidazolyl)butylamino]ethylene.

(ii) A solution of the methylthio compound (2.0 g) in ethanolic methylamine (33% w/v, 2 ml) was set aside overnight at room temperature and then heated under reflux for 15 min. From the reaction mixture was isolated the title compound (1.9 g).

EXAMPLE 9

1-Nitro-2-methylamino-2-[3-(2-imidazolythio)-propylamino]ethylene

By the procedure of Example 8 (i), 2-(3-aminopropylthio)imidazole (from the dihydrobromide (3.8 g)) is reacted with 1-nitro-2,2-bis-methylthioethylene (2.0 g) to give 1-nitro-2-methylthio-2-[3-(2-imidazolythio)-propylamino]ethylene which, on treatment with methylamine according to the procedure of Example 8(ii) gives the title compound.

EXAMPLE 10

1-Nitro-2-methylamino-2-[2-(2-(4-imidazolyl)ethylthio)ethylamino]ethylene

4-[2-(2-Aminoethylthio)ethyl]imidazole (from the dihydrobromide (4.0 g)) is reacted with 1-nitro-2,2-bis-methylthioethylene (2.0 g) by the procedure of Example 8(i) and the resultant 1-nitro-2-methylthio-2-[2-(2-(4-imidazolyl)ethylthio)ethylamino]ethylene is treated with methylamine according to the procedure of Example 8(ii) to yield the title compound.

EXAMPLE 11

When 4-bromo-5-[(2-aminoethyl)thiomethyl]imidazole (from the dihydrobromide (4.8 g)) is reacted with 1-nitro-2,2-bis-methylthioethylene (2.0 g) according to the procedure of Example 8(i) and the resultant 1-nitro-2-methylthio-2-[2-((4-bromo-5-imidazolyl)methylthio)ethylamino]ethylene treated with methylamine by the procedure of Example 8(ii) there is produced 1-nitro-2-methylamino-2-[2-((4-bromo-5-imidazolyl)methylthio)ethylamino]ethylene.

EXAMPLE 12

1-Nitro-2-methylamino-2-[2-((2-amino-4-imidazolyl)-methylthio)ethylamino]ethylene Freshly prepared sodium amalgam (90 g) is added over 75 minutes to a stirred solution of serine ethyl ester dihydrochloride (3.0 g) in water/ethanol (2:1), the temperature being maintained within the range of from $-12°$ to $-10°$ and the pH at about 2.5 by the addition of 5 N hydrochloric acid. After a further 45 minutes the mixture is allowed to warm to 10° and the precipitated free mercury is removed. Cyanamide is added and the mixture warmed to 50° for 30 minutes, left at 0° for 18 hours and evaporated to dryness. After washing with ether to remove any unchanged cyanamide, the residue is extracted with hot ethanol and heated with hot ethanolic picric acid. Concentration and cooling of the solution gives 2-amino-4-hydroxymethylimidazole picrate.

Reaction of 2-amino-4-hydroxymethylimidazole hydrochloride (which is obtained by treating the picrate salt with hydrochloric acid) with cysteamine hydrochloride and reaction of the resulting 2-amino-4-[(2-aminoethyl)thiomethyl]imidazole with 1-nitro-2,2-bis-methylthioethylene according to the procedure of Example 8(i) gives 1-nitro-2-methylthio-2-[2-((2-amino-4-imidazolyl)methylthio)ethylamino]ethylene. Finally, reaction with methylamine by the procedure of Example 8(ii) produces the title compound.

EXAMPLE 13

In the procedure of Example 4, replacement as starting material of phenylsulphonylacetonitrile by
(4-chlorophenyl)sulphonylacetonitrile
(3,4-dichlorophenyl)sulphonylacetonitrile
(4-methylphenyl)sulphonylacetonitrile results in the formation of the following products:
1-(4-chlorobenzene)sulphonyl-2-amino[2-((4-methyl-5-imidazolyl)methylthio)ethylamino]ethylene 1-(3,4-dichlorobenzene)sulphonyl-2-amino-[2-((4-methyl-5-imidazolyl)methylthio)ethylamino]ethylene.
1-(4-methylbenzene)sulphonyl-2-amino-[2-((4-methyl-5-imidazolyl)methylthio)ethylamino]ethylene.

EXAMPLE 14

By using diphenylsulphonylmethane as the starting material in place of malononitrile in the procedure of Example 1 (a) (i) there is produced 1,1-diphenylsulphonyl-2-methylthio-2-methylamino ethylene and when this is reacted with 4-methyl-5-[(2-aminoethyl)thiomethyl]imidazole according to the procedure of Example 1 (a)(ii), the resultant product is 1,1-diphenylsulphonyl-2-methylamino-2-[2-((4-methyl-5-imidazolyl)methylthio)ethylamino]ethylene.

By the same procedure, starting from
nitroacetonitrile,
phenylsulphonylnitromethane and
phenylsulphonylacetonitrile the following products may be produced
1-cyano-1-nitro-2-methylamino-2-[2-((4-methyl-5-imidazolyl)methylthio)ethylamino]ethylene,
1-nitro-1-phenylsulphonyl-2-methylamino-2-[2-((4-methyl-5-imidazolyl)methylthio)ethylamino]ethylene and
1-cyano-1-phenylsulphonyl-2-methylthio-2-[2-((4-methyl-5-imidazolyl)methylthio)ethylamino]ethylene.

EXAMPLE 15

Reaction of 1-nitro-2-methylthio-2-[2-((4-methyl-5-imidazolyl)methylthio)ethylamino]ethylene wth an excess of 2-[(2-aminoethyl)thiomethyl]thiazole according to the procedure of Example 3, results in the production of 1-nitro-2-[2-((4-methyl-5-imidazolyl)methylthio)ethylamino]-2-[2-(2-thiazolylmethylthio)ethylamino]ethylene, m.p. 119°-120° (from acetonitrile).

By the same procedure, reaction of 1-nitro-2-methylthio-2-[2-((4-methyl-5-imidazolyl)methylthio)ethylamino]ethylene with the following compounds
3-[(2-aminoethyl)thiomethyl]isothiazole (prepared by the method of Example 72),
4-(4-aminobutyl)imidazole,
4-bromo-5-[(2-aminoethyl)thiomethyl]imidazole,
2-(3-aminopropylthio)oxazole (prepared by the method of Example 19),
3-[(2-aminoethyl)thiomethyl]isoxazole (prepared by the method of Example 31),
3-[(2-aminoethyl)thiomethyl]-1,2,4-triazole and
2-amino-5-[(2-aminoethyl)thiomethyl]-1,3,4-thiadiazole yields respectively the products:
1-nitro-2-[2-((4-methyl-5-imidazolyl)methylthio)ethylamino]-2-[2-(3-isothiazolylmethylthio)ethylamino]ethylene,
1-nitro-2-[2-((4-methyl-5-imidazolyl)methylthio)ethylamino]-2-[4-(4-imidazolyl)butylamino]ethylene, 1-nitro-2-[2-((4-methyl-5-imidazolyl)methylthio)e-
thylamino]-2-[2-((4-bromo-5-imidazolyl)methylthi-
o)ethylamino]ethylene, 1-nitro-2-[2-((4-methyl-5-imidazolyl)methylthio)e-
thylamino]-2-[3-(2-oxazolylthio)propylamino]ethy-
lene, 1-nitro-2-[2-((4-methyl-5-imidazolyl)methylthio)e-
thylamino]-2-[2-(3-isoxazolylmethylthio)e-
thylamino]ethylene, 1-nitro-2-[2-((4-methyl-5-imidazolyl)methylthio)e-
thylamino]-2-[2-(3-(1,2,4)-triazolylmethylthio)e-
thylamino]ethylene and 1-nitro-2-[2-((4-methyl-5-imidazolyl)methylthio)e-
thylamino]-2-[2-((2-amino-5-(1,3,4)-thiadiazolyl)-
methylthio)ethylamino]ethylene.

EXAMPLE 16

When a solution of
1-nitro-2-methylamino-2-[2-(4-methyl-5-imidazolyl)-
methylthio)ethylamino]ethylene in acetone is treated with ion-exchange resin IRA 400 in the chloride form the corresponding hydrochloride addition salt is formed.

Similarly, by using the above procedure with ion-exchange resin IRA 400 which has been converted to the bromide, iodide and sulphate respectively the hydrobromide, hydriodide and hydrogen sulphate addition salts of 1-nitro-2-methylamino-2-[2-(4-methyl-5-imidazolyl)methylthio)ethylamino]ethylene may be produced.

EXAMPLE 17

| Ingredients | Amounts |
| --- | --- |
| 1-Nitro-2-methylamino-2-[2-(4-methyl-5-imidazolylmethylthio)ethylamino]ethylene | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 18

| Ingredients | Amounts |
| --- | --- |
| 1-Nitro-2,2-bis-[2-(4-methyl-5-imidazolylmethylthio)ethylamino]ethylene | 200 mg |
| Lactose | 100 mg |

The ingredients are screened, mixed and filled into a hard gelatin capsule.

EXAMPLE 19

1-Nitro-2-methylamino-2-[3-(2-oxazolylthio)-
propylamino]ethylene (i) Hydrochloric acid (90 ml) was added to potassium thiocyanate in ethanol (1.8 l.) with stirring. Following filtration from inorganic material, glycollaldehyde (35.9 g) was added and the resulting solution was heated under reflux for 24 hours. Concentration, followed by cooling afforded a white solid, which following recystallisation from ethanol afforded oxazole-2-thiol (30 g), m.p. 143°–144°.

(ii) 3-Bromopropylphthalimide (13.4 g) was added to a stirred solution of sodium ethoxide (from 1.15 g sodium) and oxazole-2-thiol (5.1 g) in ethanol (100 ml).

The resultant solution was heated under reflux for 2.5 hours and concentrated under reduced pressure. The residue was triturated with water (100 ml) to afford 2-(3-phthalimidopropylthio)oxazole (14 g), m.p. 101°. Recrystallisation from ethanol gave the pure oxazole, m.p. 102°–103°.

(iii) Hydrazine hydride (5.3 g) was added carefully to a solution of 2-(3-phthalimidopropylthio)oxazole (10 g) in ethanol (173 ml) with stirring. The solution was then heated under reflux for 25 minutes. After cooling, and filtration from phthalhydrazide, the filtrate was concentrated under reduced pressure and the residue was re-evaporated with ethanol to yield crude 2-(3-aminopropylthio)oxazole.

(iv) By the procedure of Example 8(i), 2-(3-aminopropylthio)oxazole (2.1 g) is reacted with 1-nitro-2,2-bis-methylthioethylene (2.0 g) to give 1-nitro-2-methylthio-2-[3-(2-oxazolylthio)propylamino]ethylene (2.1 g) which, on reaction with methylamine by the procedure of Example 8(ii) gives the title product (1.8 g).

EXAMPLE 20

1-Nitro-2-methylamino-2-[3-(4-methyl-2-oxazolylthio)-
propylamino]ethylene (i) The reaction of 4-methyloxazole-2-thiol (5.8 g) with 3-bromopropylphthalimide (13.4 g) using the conditions described in Example 19 afforded 4-methyl-2-(3-phthalimidopropylthio)oxazole (14 g), m.p. 92°–93° (ethanol-ether).

(ii) Treatment of the phthalimide compound (3.0 g) with hydrazine (1.53 g) followed by reaction of the product directly with 1-nitro-2,2-bis-methylthioethylene (2.2 g) and then with methylamine under the conditions described in Example 8 afforded the title product.

EXAMPLE 21

1-Nitro-2-methylamino-2-[2-((4-methyl-5-oxazolyl)me-
thylthio)ethylamino]ethylene.

(i) Phthalimidoethanethiol (2 g) was added portionwise with stirring to a solution of sodium ethoxide (prepared from 0.23 g of sodium) in ethanol (20 ml) at 0° under a nitrogen atmosphere. After stirring at 0° for a further 2½ hours, the resulting yellow solution was cooled with an ice-salt bath and a solution of 4-methyl-5-chloromethyloxazole (0.86 g) in ethanol (5 ml) was added dropwise over 10 minutes. After addition the mixture was stirred at room temperature overnight, then acidified with ethanolic hydrogen chloride and evaporated to dryness. Addition of water precipitated unreacted phthalimidoethanethiol (0.6 g) which was removed by filtration. The filtrate was concentrated and basified with aqueous sodium bicarbonate solution to furnish a white precipitate which, on recrystallisation from aqueous ethanol, gave 4-methyl-5-[(2-phthalimidoethyl)thiomethyl]oxazole (0.75 g). A stirred mixture of this phthalimido derivative (0.62 g) in aqueous hydrobromic acid (40 ml. 18%) was heated under reflux overnight. After cooling to 0°, the resulting clear solution was filtered and the filtrate evaporated to dryness. Recrystallisation of the residue from ethanol gave 4-methyl-5-[(2-aminoethyl)thiomethyl]oxazole dihydrobromide (0.52 g).

(ii) Reacting 4-methyl-5-[(2-aminoethyl)thiomethyl]oxazole with 1-nitro-2,2-bis-methylthioethylene and then with methylamine by the procedure of Example 8 gives the title product.

EXAMPLE 22

Using 5-(2-chloroethyl)-4-methyloxazole as starting material in the procedure of Example 21 the product is 1-nitro-2-methylamino-2-[2-(2-(4-methyl-5-oxazolyl)ethyl)thioethylamino]ethylene.

Also, using 2-amino-5-(2-chloroethyl)oxazole (prepared by reacting 2-amino-5-(2-hydroxyethyl)oxazole with thionyl chloride) in the procedure of Example 21 gives 1-nitro-2-methylamino-2-[2-(2-(2-amino-5-oxazolyl)ethyl)thioethylamino]ethylene.

EXAMPLE 23

1-Nitro-2-methylamino-2-[2-((5-chloro-2-methyl-4-oxazolyl)methylthio)ethylamino]ethylene Reduction of 5-chloro-2-methyl-4-oxazolecarboxylic acid with diborane to the corresponding 4-hydroxymethyl compound, conversion of this to the 4-chloromethyl compound and use of this chloromethyl compound as the starting material in the procedure of Example 21 gives the title compound.

EXAMPLE 24

1,1-Dicyano-2-[3-(2-oxazolylthio)propylamino]-2-[2-((4-methyl-5-imidazolyl)methylthio)ethylamino]ethylene (i) Reaction of malononitrile with carbon disulphide in the presence of alcoholic sodium methoxide and treatment of the product with methyl iodide (see Berichte, 1962, 95, 2861) yields 1,1-dicyano-2,2-bis-methylthioethylene.

(ii) Reaction of 4-methyl-5-[(2-aminoethyl)thiomethyl]imidazole with 1,1-dicyano-2,2-bis methylthioethylene by the procedure of Example 8(i) yields 1,1-dicyano-2-methylthio-2-[2-((4-methyl-5-imidazolyl)methylthio)ethylamino]ethylene.

(iii) Reaction of this methylthio compound with 2-(3-aminopropyl)thiooxazole by the procedure of Example 1(a)(ii) gives the title compound.

EXAMPLE 25

1-Cyano-2-[3-(2-oxazolylthio)propylamino]-2-[2-((4-methyl-5-imidazolyl)methylthio)ethylamino]ethylene Reaction of 1-cyano-2,2-bis methoxyethylene (J.A.C.S., 1949, 71, 47) with 4-methyl-5-[(2-aminoethyl)thiomethyl]imidazole by the procedure of Example 8(i) yields 1-cyano-2-methoxy-2-[2-((4-methyl-5-imidazolyl)methylthio)ethylamino]ethylene.

(ii) Reaction of this methylthio compound with 2-(3-aminopropylthio)oxazole by the procedure of Example 1(a)(ii) gives the title compound.

EXAMPLE 26

(i) Reaction of methylphenylsulphone with carbon disulphide under strongly basic conditions and treatment of the product with methyliodide yields 1-benzenesulphonyl-2,2-bis-methylthioethylene.

(ii) When 1-benzenesulphonyl-2,2-bis-methylthioethylene is reacted in the procedure of Example 8(i) with:

5-[(2-aminoethyl)thiomethyl]-4-methylimidazole the product is:

1-benzenesulphonyl-2-methylthio-2-[2-((4-methyl-5-imidazolyl)methylthio)ethylamino]ethylene.

(iii) Reaction of this methylthio compound with 2-(3-aminopropylthio)oxazole by the procedure of Example 1(a)(ii) gives:

1-benzenesulphonyl-2-[3-(2-oxazolylthio)propylamino]-2-[2-((4-methyl-5-imidazolyl)methylthio)ethylamino]ethylene. When, in place of methylphenylsulphone, the following sulphones are used as the starting materials:

methyl-(4-chlorophenyl)sulphone,
methyl-(3,4-dichlorophenyl)sulphone and
methyl-(4-methylphenyl)sulphone, the following products are produced respectively:

1-(4-chlorobenzene)sulphonyl-2-[3-(2-oxazolylthio)propylamino]-2-[2-((4-methyl-5-imidazolyl)methylthio)ethylamino]ethylene, 1-(3,4-dichlorobenzene)sulphonyl-2-[3-(2-oxazolylthio)propylamino]-2-[2-((4-methyl-5-imidazolyl)methylthio)ethylamino]ethylene and 1-(4-methylbenzene)sulphonyl-2-[3-(2-oxazolylthio)propylamino]-2-[2-((4-methyl-5-imidazolyl)methylthio)ethylamino]ethylene.

EXAMPLE 27

1-Nitro-2-ethylamino-2-[3-(2-oxazolylthio)propylamino]ethylene

Reaction of 1-nitro-2-methylthio-2-[3-(2-oxazolylthio)propylamino]ethylene (see Example 19 (iv)) with ethylamine by the procedure of Example 8(ii) gives the title product.

EXAMPLE 28

Reaction of 1-nitro-2-methylthio-2-[3-(2-oxazolylthio)propylamino]ethylene in the procedure of Example 3 with an excess of the following compounds:

2-(3-aminopropylthio)oxazole,
3-[(2-aminoethyl)thiomethyl]isoxazole (prepared by the method of Example 30),
3-[(2-aminoethyl)thiomethyl]-1,2,4-triazole,
2-[(2-aminoethyl)thiomethyl]thiazole,
3-[(2-aminoethyl)thiomethyl]isothiazole (prepared by the method of Example 72) and
2-amino-5-[(2-aminoethyl)thiomethyl]-1,3,4-thiadiazole gives the following products respectively:

1-nitro-2,2-bis-[3-(2-oxazolylthio)propylamino]ethylene, 1-nitro-2-[3-(2-oxazolylthio)propylamino]-2-[2-(3-isoxazolylmethylthio)ethylamino]ethylene, 1-nitro-2-[3-(2-oxazolylthio)propylamino]-2-[2-(3-(1,2,4)-triazolylmethylthio)ethylamino]ethylene, 1-nitro-2-[3-(2-oxazolylthio)propylamino]-2-[2-(2-thiazolylmethylthio)ethylamino]ethylene, 1-nitro-2-[3-(2-oxazolylthio)propylamino]-2-[2-(3-isothiazolylmethylthio)ethylamino]ethylene and 1-nitro-2-[3-(2-oxazolylthio)propylamino]-2-[2-((2-amino-5-(1,3,4)-thiadiazolyl)methylthio)ethylamino]ethylene.

EXAMPLE 29

| Ingredients | Amounts |
| --- | --- |
| 1-Nitro-2-[3-(2-oxazolylthio)propylamino]-2-[2-((4-methyl-5-imidazolyl)methylthio)ethylamino]ethylene | 150 mg |
| Sucrose | 75 mg |
| Starch | 25 mg |
| Talc | 5 mg |

| Ingredients | Amounts |
| --- | --- |
| Stearic Acid | 2 mg |

The ingredients are mixed and filled into a hard gelatin capsule.

EXAMPLE 30

| Ingredients | Amounts |
| --- | --- |
| 1-Nitro-2-[3-(2-oxazolylthio)propylamino]-2-[2-((4-methyl-5-imidazolyl)methylthio)-ethylamino]ethylene | 200 mg |
| Lactose | 100 mg |

The ingredients are mixed and filled into a hard gelatin capsule.

EXAMPLE 31

1-Nitro-2-methylamino-2-[2-(3-isoxazolylmethylthio)ethylamino]ethylene (i) A solution of 3-chloromethylisoxazole (5.8 g) and cysteamine hydrochloride (6.25 g) in aqueous hydrobromic acid (48%, 100 ml) was heated under reflux for 6 hours. Concentration in the presence of water and subsequently n-propanol, followed by recrystallisation of the residue from isopropyl alcohol-ethanol afforded 3-[(2-aminoethyl)thiomethyl]isoxazole hydrobromide, m.p. 131°–133°.

(Found: Br, 33.6; S, 13.7. $C_6H_{10}N_2OS \cdot HBr$ requires: Br, 33.4: S, 13.4).

(ii) By the procedure of Example 8(i), 3-[(2-aminoethyl)thiomethyl]isoxazole (from the hydrobromide (3.7 g)) is reacted with 1-nitro-2,2-bis-methylthioethylene (3.5 g) to give 1-nitro-2-methylthio-2-[2-(3-isoxazolylmethylthio)ethylamino]ethylene (3.6 g) which, on reaction with methylamine by the procedure of Example 8(ii) gives the title product (3.0 g).

EXAMPLE 32

Using the following chloromethylisoxazoles (prepared from the corresponding hydroxymethylisoxazoles by treatment thereof with thionyl chloride) as starting materials in the procedure of Example 31:
3-chloromethyl-5-methylisoxazole,
3-bromo-5-chloromethylisoxazole and
4-(2-chloroethyl)-5-methylisoxazole the products are, respectively:
1-nitro-2-methylamino-2-[2-(5-methyl-3-isoxazolylmethylthio)ethylamino]ethylene,
1-nitro-2-methylamino-2-[2-(3-bromo-5-isoxazolylmethylthio)ethylamino]ethylene and
1-nitro-2-methylamino-2-[2-(2-(5-methyl-4-isoxazolyl)ethylthio)ethylamino]ethylene.

EXAMPLE 33

Using, in the procedure of Example 31, 3-mercaptopropylamine in place of cysteamine, the product is 1-nitro-2-methylamino-2-[3-(3-isoxazolylmethylthio)propylamino]ethylene.

EXAMPLE 34

1,1-Dicyano-2-methylamino-2-[2-(3-isoxazolylmethylthio)ethylamino]ethylene

By the procedure of Example 1(ii), reacting 3-[(2-aminoethyl)thiomethyl]isoxazole with 1,1-dicyano-2-methylthio-2-methylaminoethylene gives the title compound.

EXAMPLE 35

1-Cyano-2-methylamino-2-[2-(3-isoxazolylmethylthio)ethylamino]ethylene.

By the same procedure as Example 7, using as starting material 3-[(2-aminoethyl)thiomethyl)isoxazole, the title compound is prepared.

EXAMPLE 36

Reaction of 3-[(2-aminoethyl)thiomethyl]isoxazole by the procedure of Example 4 with the following acetonitriles:
phenylsulphonylacetonitrile,
(4-chlorophenyl)sulphonylacetonitrile,
(3,4-dichlorophenyl)sulphonylacetonitrile and
(4-methylphenyl)sulphonylacetonitrile
results in the formation of the following products, respectively:
1-benzenesulphonyl-2-amino-2-[2-(3-isoxazolylmethylthio)ethylamino]ethylene,
1-(4-chlorobenzene)sulphonyl-2-amino-2-[2-(3-isoxazolylmethylthio)ethylamino]ethylene,
1-(3,4-dichlorobenzene)sulphonyl-2-amino-2-[2-(3-isoxazolylmethylthio)ethylamino]ethylene and
1-(4-methylbenzene)sulphonyl-2-amino-2-[2-(3-isoxazolylmethylthio)ethylamino]ethylene.

EXAMPLE 37

1-Nitro-2-ethylamino-2-[2-(3-isoxazolylmethylthio)ethylamino]ethylene

Reaction of 1-nitro-2-methylthio-2-[2-(3-isoxazolylmethylthio)ethylamino]ethylene (see Example 31(ii)) with ethylamine by the procedure of Example 8(ii) gives the title product.

EXAMPLE 38

Reaction of 1-nitro-2-methylthio-2-[2-(3-isoxazolylmethylthio)ethylamino]ethylene in the procedure of Example 3, with an excess of the following compounds:
3-[(2-aminoethyl)thiomethyl]isoxazole,
3-[(2-aminoethyl)thiomethyl]-1,2,4-triazole,
2-[(2-aminoethyl)thiomethyl]thiazole,
3-[(2-aminoethyl)thiomethyl]isothiazole (prepared by the method of Example 72) and
2-amino-5-[(2-aminoethyl)thiomethyl]-1,3,4-thiadiazole, gives the following products respectively:
1-nitro-2,2-bis-[2-(3-isoxazolylmethylthio)ethylamino]ethylene,
1-nitro-2-[2-(3-isoxazolylmethylthio)ethylamino]-2-[2-(3-(1,2,4)-triazolylmethylthio)ethylamino]ethylene,
1-nitro-2-[2-(3-isoxazolylmethylthio)ethylamino]-2-[2-(2-thiazolylmethylthio)ethylamino]ethylene,
1-nitro-2-[2-(3-isoxazolylmethylthio)ethylamino]-2-[2-(3-isothiazolylmethylthio)ethylamino]ethylene and
1-nitro-2-[2-(3-isoxazolylmethylthio)ethylamino]-2-[2-((2-amino-5-(1,3,4)-thiadiazolyl)methylthio)ethylamino]ethylene.

EXAMPLE 39

| Ingredients | Amounts |
| --- | --- |
| 1-Nitro-2-methylamino-2-[2-(3-isoxazolylmethylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 40

| Ingredients | Amounts |
| --- | --- |
| 1-Nitro-2-methylamino-2-[2-(3-isoxazolylmethylthio)ethylamino]ethylene | 200 mg |
| Lactose | 100 mg |

The ingredients are mixed and filled into a hard gelatin capsule.

EXAMPLE 41

1-Nitro-2-methylamino-2-[2-[2-(3-(1,2,4-thiazolyl)methylthio)ethylamino]ethylene By the procedure of Example 8(i) 3-[(2-aminoethyl)thiomethyl]-1,2,4-triazole (from the dihydrobromide (2.2 g)) is reacted with 1-nitro-2,2-bis-methylthioethylene (1.7 g) to give 1-nitro-2-methylthio-2-(3-(1,2,4-thiazolyl)methylthio)ethylamino]ethylene (1.5 g) which on reaction with methylamine by the procedure of Example 8(ii) gives the title product (1.3 g).

EXAMPLE 42

1-Nitro-2-methylamino-2-[2-(4-methyl-3-(1,2,4-triazolyl)methylthio)ethylamino]ethylene (i) Ethoxyacetyl chloride (57 g) was added slowly to a stirred solution of 4-methylthiosemicarbazide (53.5 g) in dry pyridine (500 ml) at 0°–5°. The mixture was allowed to attain room temperature and stirring was continued for 18 hours. Following concentration under reduced pressure the residue was treated with a solution of sodium (21.4 g) in ethanol (500 ml) and the mixture was heated under reflux for 24 hours. Following concentration and acidification with hydrochloric acid a solid was obtained. After partial concentration the solid was collected and recrystallised from ethyl acetate to give 3-ethoxymethyl-4-methyl-1,2,4-triazoline-5-thione (53 g) m.p. 137°–138°.

The thione (44 g) was desulphurised by slow addition to a solution prepared from nitric acid (75 ml) water (150 ml) and sodium nitrite (1.5 g) at 15°–20°. Following subsequent basification with sodium carbonate and concentration, the residue was extracted with ethanol-ether 1:1 and distilled to afford 3-ethoxymethyl-4-methyl-1,2,4-triazole (30 g), b.p. 154°–156°/0.05 mm. The above compound (15 g) dissolved in 48% aqueous hydrobromic acid (150 ml) was heated under reflux for 24 hours and concentrated to dryness to give a mixture of 4-methyl-3-bromoethyl-1,2,4-triazole and 4-methyl-3-hydroxymethyl-1,2,4-triazole.

(ii) This mixture was reacted directly in solution in aqueous hydrobromic acid with cysteamine hydrochloride by heating under reflux overnight. After cooling, the solution was evaporated to dryness and the residue solid washed with ethanol/ether to give 3-[(2-aminoethyl)thiomethyl]-4-methyl-1,2,4-triazole dihydrobromide, m.p. 175°–177° C.

(iii) Using 3-[(2-aminoethyl)thiomethyl]-4-methyl-1,2,4-triazole (from the dihydrobromide) as the starting material in the procedure of Example 41 yields the title product.

EXAMPLE 43

By the procedure of Example 42 (ii) and (iii), using the following triazoles as starting materials:
3-amino-5-hydroxymethyl-1,2,4-triazole,
3-bromo-5-hydroxymethyl-1,2,4-triazole and
3-(2-chloroethyl)-1,2,4-triazole the products are, respectively,
1-nitro-2-methylamino-2-[2-(3-amino-5-(1,2,4-triazolyl)methylthio)ethylamino]ethylene,
1-nitro-2-methylamino-2-[2-(3-bromo-5-(1,2,4-triazolyl)methylthio)ethylamino]ethylene and
1-nitro-2-methylamino-2-[2-(2-(3-(1,2,4-triazolyl)ethyl)thio)ethylamino]ethylene.

EXAMPLE 44

1-Nitro-2-[2-((5-hydroxy-4-1,2,3-triazolyl)methylthio)ethylamino]2-[2-((4-methyl-5-imidazolyl)methylthio)ethylamino]ethylene Alkaline hydrolysis of 5-hydroxy-4-carboethoxy-(1,2,3)-triazole to the corresponding carboxylic acid, conversion of the acid to the methyl ester and reduction of this ester with lithium aluminium hydride in tetrahydrofuran gives 5-hydroxy-4-hydroxymethyl-(1,2,3)-triazole. This compound is used as the starting material in the procedure of Example 42(ii) to give 4-[2-aminoethyl)thiomethyl]-5-hydroxy-1,2,3-triazole which, on reaction with 1-nitro-2-methylthio-2-[2-((4-methyl-5-imidazolyl)methylthio)ethylamino]ethylene by the procedure of Example 3 yields the title product.

EXAMPLE 45

1-Nitro-2-methylamino-2-[4-(3-1,2,4-triazolyl)-butylamino]ethylene

Use of 3-(4-aminobutyl)-1,2,4-triazole (from the dihydrochloride) as the starting material in the procedure of Example 8(i) and (ii) results in the production of the title compound.

EXAMPLE 46

1-Nitro-2-methylamino-2-[3-(3-(1,2,4-triazolyl)thio)-propylamino]ethylene (i) A solution of 3-mercapto-1,2,4-triazole and 3-aminopropanol in hydrobromic acid is heated under reflux for 24 hours. The reaction mixture is evaporated to dryness and the residue recrystallised from ethanol/ether to give 3-(3-aminopropylthio)-1,2,4-triazole dihydrobromide.

(ii) Conversion of this dihydrobromide to the free base which is then used as the starting material in the procedure of Example 8 (i) and 8 (ii) yields the title product.

EXAMPLE 47

1,1-Dicyano-2-methylamino-2-[2-(3-(1,2,4-triazolyl)methylthio)ethylamino]ethylene By the procedure of Example 1(ii), reacting 3-[(2-aminoethyl)thiomethyl]-1,2,4-triazole with 1,1-dicyano- 2-methylthio-2-methylaminoethylene gives the title compound.

EXAMPLE 48

1-Cyano-2-methylamino-2-[2-(3-(1,2,4-triazolyl)methylthio)ethylamino]ethylene

By the same procedure as Example 7, using as starting material 3-[(2-aminoethyl)thiomethyl]-1,2,4-triazole, the title compound is prepared.

EXAMPLE 49

Reaction of 3-[(2-aminoethyl)thiomethyl]-1,2,4-triazole by the procedure of Example 4 with the following acetonitriles:
 phenylsulphonylacetonitrile,
 (4-chlorophenyl)sulphonylacetonitrile,
 (3,4-dichlorophenyl)sulphonylacetonitrile and
 (4-methylphenyl)sulphonylacetonitrile
results in the formation of the following products, respectively:
 1-benzenesulphonyl-2-amino-2-[2-(3-(1,2,4-triazolyl)-methylthio)ethylamino]ethylene,
 1-(4-chlorobenzene)sulphonyl-2-amino-2-[2-(3-(1,2,4-triazolyl)methylthio)ethylamino]ethylene,
 1-(3,4-dichlorobenzene)sulphonyl-2-amino-2-[2-(3-(1,2,4-triazolyl)methylthio)ethylamino]ethylene and
 1-(4-methylbenzene)sulphonyl-2-amino-2-[2-(3-(1,2,4-triazolyl)methylthio)ethylamino]ethylene.

EXAMPLE 50

1-Nitro-2-ethylamino-2-[2-(3-(1,2,4-triazolyl)methylthio)ethylamino]ethylene

Reaction of 1-nitro-2-methylthio-2-[2-(3-(1,2,4-triazolyl)methylthio)ethylamino]ethylene (see Example 41) with ethylamine by the procedure of Example 8(ii) gives the title product.

EXAMPLE 51

Reaction of 1-nitro-2-methylthio-2-[2-(3-(1,2,4-triazolyl)methylthio)ethylamino]ethylene in the procedure of Example 2(ii) with an excess of the following compounds:
 3-[(2-aminoethyl)thiomethyl]1,2,4-triazole,
 2-[(2-aminoethyl)thiomethyl]thiazole,
 3-[(2-aminoethyl)thiomethyl]isothiazole (prepared by the method of Example 72 and
 2-amino-5-[(2-aminoethyl)thiomethyl]-1,3,4-thiadiazole gives the following products respectively:
 1-nitro-2,2-bis-[2-(3-(1,2,4-triazolyl)methylthio)ethylamino]ethylene,
 1-nitro-2-[2-(3-(1,2,4-triazolyl)methylthio)ethylamino]-2-[2-(2-thiazolylmethylthio)ethylamino]ethylene,
 1-nitro-2-[2-(3-(1,2,4-triazolyl)methylthio)ethylamino]-2-[2-(3-isothiazolylmethylthio)ethylamino]ethylene and
 1-nitro-2-[2-(3-(1,2,4-triazolyl)methylthio)ethylamino]2-[2-((2-amino-5-(1,3,4)thiadiazolyl)methylthio)ethylamino]ethylene.

EXAMPLE 52

| Ingredients | Amounts |
| --- | --- |
| 1-Nitro-2-methylamino-2-[2-(3-(1,2,4-triazolyl)-methylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 53

| Ingredients | Amounts |
| --- | --- |
| 1-Nitro-2-methylamino-2-[2-(3-(1,2,4-triazolyl)-methylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 54

1-Nitro-2,2-bis-[4-(2-thiazolyl)butylamino]ethylene

A mixture of 2-(4-aminobutyl)thiazole (from the dihydrobromide (10.0 g) and 1-nitro-2,2-bis-methylthioethylene (3.0 g) in ethanol (20 ml) is heated under reflux for 3 hours. Concentration and treatment of the residue with ether affords the title compound, m.p. 109°–110° (ethanol-ether).

EXAMPLE 55

1-Nitro-2-methylamino-2-[2-(2-thiazolylmethylthio)ethylamino]ethylene (i) By the procedure of Example 8(i), 2-[(2-aminoethyl)thiomethyl]thiazole (from the dihydrobromide, 4.0 g) is reacted with 1-nitro-2,2-bis methylthioethylene (2.0 g) to give 1-nitro-2-methylthio-2-[(2-thiazolylmethylthio)ethylamino]ethylene, m.p. 63°–64°.

(ii) Reaction of 1-nitro-2-methylthio-2-[2-(2-thiazolylmethylthio)ethylamino]ethylene with methylamine according to the process of Example 8(ii) yielded the title compound, m.p. 103°–104°. (from ethanol ether).

Found: C, 39.4; H, 5.2; N, 20.2% $C_9H_{14}N_4O_2S_2$ requires: C, 39.4; H, 5.1; N, 20.4%).

EXAMPLE 56

1-Nitro-2-methylamino-2-[2-(4-thiazolylmethylthio)ethylamino]ethylene

When 4-[(2-aminoethyl)thiomethyl]thiazole (from the dihydrobromide) is used as the starting material in the procedure of Example 55, the title compound is produced.

EXAMPLE 57

1-Nitro-2-methylamino-2-[3-(2-thiazolylthio)-propylamino]ethylene

Using 2-(3-aminopropylthio)thiazole (from the dihydrobromide) as the starting material in the procedure of Example 55 gives the title compound.

EXAMPLE 58

1-Nitro-2-methylamino-2-[2-(5-thiazolylmethylthio)ethylamino]ethylene

When 5-[(2-aminoethyl)thiomethyl]thiazole (from the dihydrobromide) is used as the starting material in the procedure of Example 55, the title compound is produced.

EXAMPLE 59

1-Nitro-2-methylamino-2-[2-((2-amino-4-thiazolyl)methylthio)ethylamino]ethylene

Using 2-amino-4-[(2-aminoethyl)thiomethyl]thiazole as the starting material in the procedure of Example 55 gives the title compound.

EXAMPLE 60

Using the following thiazoles as starting materials in the procedure of Example 42 (ii) and 42 (iii):
2-hydroxymethyl-4-methylthiazole,
4-chloromethyl-2-methylthiazole,
2-chloro-4-chloromethylthiazole and
4-(2-chloroethyl)thiazole
the products are, respectively:
 1-nitro-2-methylamino-2-[2-((4-methyl-2-thiazolyl)methylthio)ethylamino]ethylene,
 1-nitro-2-methylamino-2-[2-((2-methyl-4-thiazolyl)methylthio)ethylamino]ethylene,
 1-nitro-2-methylamino-2-[2-((2-chloro-4-thiazolyl)methylthio)ethylamino]ethylene and
 1-nitro-2-methylamino-2-[2-(2-(4-thiazolyl)ethyl)thioethylamino]ethylene.

EXAMPLE 61

1-Nitro-2-[2-((2-hydroxy-4-thiazolyl)methylthio)ethylamino]-2-[2-((4-methyl-5-imidazolyl)methylthio)ethylamino]ethylene 2-Hydroxy-4-thiazolecarboxylic acid is converted to the methyl ester and the ester is reduced with lithium aluminium hydride in tetrahydrofuran to give 2-hydroxy-4-hydroxymethylthiazole. This compound is used as the starting material in the procedure of Example 42 (ii) to give 2-hydroxy-4-[(2-aminoethyl)thiomethyl]thiazole which, on reaction with 1-nitro-2-methylthio-2-[2-((4-methyl-5-imidazolyl)methylthio)ethylamino]ethylene by the procedure of Example 3 yields the title compound.

EXAMPLE 62

1-Nitro-2-methylamino-2-[4-(2-thiazolyl)butylamino]ethylene

Using 2-(4-aminobutyl)thiazole as the starting material in the procedure of Example 55 results in the production of the title compound, m.p. 144°–145° (ethanol-ether).

EXAMPLE 63

1,1-Dicyano-2-methylamino-2-[2-(2-thiazolylmethylthio)ethylamino]ethylene

By the procedure of Example 1(ii), reacting 2-[(2-aminoethyl)thiomethyl]thiazole with 1,1-dicyano-2-methylthio-2-methylaminoethylene gives the title compound.

EXAMPLE 64

1-Cyano-2-methylamino-2-[2-(2-thiazolylmethylthio)ethylamino]ethylene

By the same procedure as Example 7, using as starting material 2-[(2-aminoethyl)thiomethyl]thiazole, the title compound is prepared.

EXAMPLE 65

Reaction of 2-[(2-aminoethyl)thiomethyl]thiazole by the procedure of Example 4 with the following acetonitriles:
phenylsulphonylacetonitrole,
(4-chlorophenyl)sulphonylacetonitrile,
(3,4-dichlorophenyl)sulphonylacetonitrile and
(4-methylphenyl)sulphonylacetonitrile
results in the formation of the following products, respectively:
 1-benzenesulphonyl-2-amino-2-[2-(2-thiazolylmethylthio)ethylamino]ethylene,
 1-(4-chlorobenzene)sulphonyl-2-amino-2-[2-(2-thiazolylmethylthio)ethylamino]ethylene,
 1-(3,4-dichlorobenzene)sulphonyl-2-amino-2-[2-(2-thiazolylmethylthio)ethylamino]ethylene and
 1-(4-methylbenzene)sulphonyl-2-amino-2-[2-(2-thiazolylmethylthio)-ethylamino]ethylene

EXAMPLE 66

1-Nitro-2-ethylamino-2-[2-(2-thiazolylmethylthio)ethylamino]ethylene

Reaction of 1-nitro-2-methylthio-2-[2-(2-thiazolylmethylthio)ethylamino]ethylene (see Example 55(i)) with ethylamine by the procedure of Example 8(ii) gives the title product, m.p. 115°–116° (from water).

EXAMPLE 67

1-Nitro-2,2-bis-[2-(2-thiazolylmethylthio)ethylamino]ethylene

A mixture of 2-[(2-aminoethyl)thiomethyl]thiazole (from the dihydrobromide 4.0 g) and 1-nitro-2,2-bis-methylthioethylene (0.99 g) was heated at 100° for 2 hours. Crystallisation of the reaction product from ethanolether yields the title compound, m.p. 50°–51°.

Found: C, 39.6; H, 4.6; N, 16.4%. $C_{14}H_{19}N_5O_2S_4$ requires: C, 40.2; H, 4.6; N, 16.8%).

EXAMPLE 68

Reaction of 1-nitro-2-methylthio-2-[(2-thiazolylmethylthio)ethylamino]ethylene in the procedure of Example 2(ii) with excess of the following compounds:
 3-[(2-aminoethyl)thiomethyl]isothiazole (prepared by the method of Example 72) and
 2-amino-5-[2-aminoethyl)thiomethyl]-1,3,4-thiadiazole
gives the following products respectively:
 1-nitro-2-[2-(2-thiazolylmethylthio)ethylamino]-2-(3-isothiazolylmethylthio)ethylamino]ethylene and
 1-nitro-2-[2-(2-thiazolylmethylthio)ethylamino]-2-[2-((2-amino-5-(1,3,4)thiadiazolyl)methylthio)ethylamino]ethylene.

EXAMPLE 69

When a solution of 1-nitro-2-[2-(2-thiazolylmethylthio)ethylamino]-2-[2-((4-methyl-5-imidazolyl)methylthio)ethylamino]ethylene in acetone is treated with ion-exchange resin IRA 400 in the chloride form the corresponding hydrochloride addition salt is formed.

Similarly, by using the above procedure with ion-exchange resin IRA 400 which has been converted to the bromide, iodide and sulphate respectively the hydrobromide, hydriodide and hydrogen sulphate addition salts of 1-nitro-2-[2-((2-2-thiazolyl)methylthio)ethylamino]-2-[2-((4-methyl-5-imidazolyl)methylthio)ethylamino]ethylene may be produced.

EXAMPLE 70

| Ingredients | Amounts |
| --- | --- |
| 1-Nitro-2-methylamino-2-[2-(2-thiazolyl-methylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 71

| Ingredients | Amounts |
| --- | --- |
| 1-Nitro-2,2-bis-[2-(2-thiazolylmethylthio)-ethylamino]ethylene | 200 mg |
| Lactose | 100 mg |

The ingredients are mixed and filled into a hard gelatin capsule.

EXAMPLE 72

1-Nitro-2-methylamino-2-[2-(3-isothiazolylmethylthio)ethylamino]ethylene (i) A solution was prepared by the gradual addition of cysteamine hydrochloride (2.03 g) to sodium (0.83 g) dissolved in ethanol (50 ml) with stirring at 0° under a nitrogen atmosphere. After stirring for 2 hours at 0° 3-bromoethylisothiazole (3.2 g) was added dropwise over 15 minutes at 0°, the reaction mixture subsequently being set aside overnight to room temperature. Following acidification to pH 3.5 with hydrochloric acid, concentration and re-evaporation with ethanol, the residue was dissolved in ethanol, filtered and concentrated to yield 3-[(2-aminoethyl)thiomethyl]isothiazole hydrochloride (3.5 g). This was converted directly to the free base by treatment with aqueous potassium carbonate and extraction with ether. The extracts were dried over magnesium sulphate, dried and concentrated to yield the amine base as an oil (1.56 g).

(ii) By the procedure of Example 8(i), this amine base is reacted with 1-nitro-2,2-bis-methylthioethylene to give 1-nitro-2-methylthio-2-[2-(3-isothiazolylmethylthio)ethylamino]ethylene, m.p. 64.5°–65.5°. Reaction of this compound with methylamine according to the process of Example 8(ii) yields the title compound, m.p. 118.5°–119.5° (from ethanol-toluene).

EXAMPLE 73

1-Nitro-2-methylamino-2-[(2-((4-bromo-3-isothiazolyl)methylthio)ethylamino]ethylene (i) The reaction of 4-bromo-3-(bromoethyl)isothiazole (8.5 g) with cysteamine (from cysteamine hydrochloride (3.76 g)) was performed under conditions similar to those described in Example 72. From the reaction there was obtained 4-bromo-3-[(2-aminoethyl)thiomethyl]isothiazole hydrobromide, which, following recrystallisation from ethanol-ether and acetonitrile, gave needles (4.05 g), m.p. 111°–112°. The amine base (2.73 g) was isolated by basification with sodium hydroxide and extraction with chloroform.

(ii) Use of the amine base as the starting material in the procedure of Example 72(ii) gives the title compound.

EXAMPLE 74

Using the following halomethylisothiazole as starting material in the procedure of Example 72:
3-bromomethyl-4-chloroisothiazole
the product is:
1-nitro-2-methylamino-2-[2-((4-chloro-3-isothiazolyl)methylthio)ethylamino]ethylene.

EXAMPLE 75

1-Nitro-2-methylamino-2-[2-((3-methyl-4-isothiazolyl)methylthio)ethylamino]ethylene.

Reacting 4-hydroxymethyl-3-methylisothiazole (3.0 g) with cysteamine hydrochloride (2.8 g) in 48% aqueous hydrobromic acid (50 ml) by the procedure of Example 42(ii) gives 3-methyl-4-[(2-aminoethyl)thiomethyl]isothiazole hydrobromide. The base is obtained by basifying with aqueous potassium carbonate, extracting with chloroform, drying the extracts over magnesium sulphate and concentrating. Using the amine (5.0 g) as the starting material in the procedure of Example 72(ii) yields the title compound.

EXAMPLE 76

1-Nitro-2-methylamino-2-[2-(2-(3-isothiazolyl)ethyl)thioethylamino]ethylene

3-Isothiazoleacetic acid is converted to the methyl ester and the ester is reduced with lithium aluminum hydride in tetrahydrofuran to give 3-(2-hydroxyethyl)isothiazole. Reacting this hydroxyethyl compound with thionyl chloride gives 3-(2-chloroethyl)isothiazole. Using 3-(2-chloroethyl)isothiazole in the procedure of Example 72 (i) and (ii), gives the title compound.

EXAMPLE 77

1-Nitro-2-methylamino-2-[3-(3-isothiazolylmethylthio)propylamino]ethylene.

When, in the procedure of Example 72, cysteamine hydrochloride is replaced by 3-mercaptopropylamine hydrochloride, the title compound is produced.

EXAMPLE 78

1,1-Dicyano-2-methylamino-2-[2-(3-isothiazolylmethylthio)ethylamino]ethylene

By the procedure of Example 1(ii), reacting 3-[(2-aminoethyl)thiomethyl]isothiazole with 1,1-dicyano-2-methylthio-2-methylaminoethylene gives the title compound.

EXAMPLE 79

1-Cyano-2-methylamino-2-[2-(3-isothiazolylmethylthio)ethylamino]ethylene.

By the same procedure as Example 7, using as starting material 3-[(2-aminoethyl)thiomethyl]isothiazole, the title compound is prepared.

EXAMPLE 80

Reaction of 3-[(2-aminoethyl)thiomethyl]isothiazole by the procedure of Example 4 with the following acetonitriles:
  phenylsulphonylacetonitrole,
  (4-chlorophenyl)sulphonylacetonitrile,
  (3,4-dichlorophenyl)sulphonylacetonitrile and
  (4-methylphenyl)sulphonylacetonitrile
results in the formation of the following products, respectively:
  1-benzenesulphonyl-2-amino-2-[2-(3-isothiazolylmethylthio)ethylamino]ethylene,
  1-(4-chlorobenzene)sulphonyl-2-amino-2-[2-(3-isothiazolylmethylthio)ethylamino]ethylene,
  1-(3,4-dichlorobenzene)sulphonyl-2-amino-2-[2-(3-isothiazolylmethylthio)ethylamino]ethylene and
  1-(4-methylbenzene)sulphonyl-2-amino-2-[2-(3-isothiazolylmethylthio)ethylamino]ethylene.

EXAMPLE 81

1-Nitro-2-ethylamino-2-[2-(3-isothiazolylmethylthio)ethylamino]ethylene

Reaction of 1-nitro-2-methylthio-2-[2-(3-isothiazolylmethylthio)ethylamino]ethylene (see Example 72(ii)) with ethylamine by the procedure of Example 8(ii) gives the title product.

EXAMPLE 82

Reaction of 1-nitro-2-methylthio-2-[2-(3-isothiazolylmethylthio)ethylamino]ethylene in the procedure of Example 2(ii) with an excess of the following compounds:
  3-[(2-aminoethyl)thiomethyl]isothiazole and
  2-amino-5-[(2-aminoethyl)thiomethyl]-1,3,4-thiadiazole
gives the following products respectively:
  1-nitro-2,2-bis-[2-(3-isothiazolylmethylthio)ethylamino]ethylene and
  1-nitro-2-[2-(3-isothiazolylmethylthio)ethylamino]-2-[2-((2-amino-5-(1,3,4)thiadiazolyl)methylthio)ethylamino]ethylene.

EXAMPLE 83

| Ingredients | Amounts |
| --- | --- |
| 1-Nitro-2-methylamino-2-[2-(3-isothiazolylmethylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 84

| Ingredients | Amounts |
| --- | --- |
| 1-Nitro-2-methylamino-2-[2-((4-bromo-3-isothiazolyl)methylthio)ethylamino]ethylene | 200 mg |
| Lactose | 100 mg |

The ingredients are mixed and filled into a hard gelatin capsule.

EXAMPLE 85

1-Nitro-2-methylamino-2-[2-((2-amino-5-(1,3,4)-thiadiazolyl)methylthio)ethylamino]ethylene (i) By the procedure of Example 8(i), 2-amino-5-(2-aminoethyl)thiomethyl-1,3,4-thiadiazole (from the dihydrobromide) is reacted with 1-nitro-2,2-bis-methylthioethylene to give 1-nitro-2-methylthio-2-[2-((2-amino-5-(1,3,4)-thiadiazolyl)methylthio)ethylamino]ethylene.

(ii) Reaction of this compound with methylamine according to the process of Example 8(ii) gives the title compound.

EXAMPLE 86

Addition of phosphonyl chloride to a mixture of thiosemicarbazide and methoxyacetic acid at 60°–95° and working up of the product yields 5-amino-2-methoxymethyl-(1,3,4)-thiadiazole, m.p. 177°–179° (from water). When this compound is diazotised and treated with cuprous bromide 5-bromo-2-methoxymethyl-(1,3,4)-thiadiazole results and reaction of this bromo compound with zinc dust in acetic acid at room temperature yields 2-methoxymethyl-(1,3,4)-thiadiazole, m.p. 30.5°–32°.

Using the following thiadiazoles as starting materials is the procedure of Example 42(ii) and 42(iii):
  5-chloro-3-chloromethyl-1,2,4-thiadiazole and
  2-methoxymethyl-1,3,4-thiadiazole
the products are, respectively:
  1-nitro-2-methylamino-2-[2-((5-chloro-3-1,2,4-thiadiazolyl)methylthio)ethylamino]ethylene and
  1-nitro-2-methylamino-2-[2-((2-1,3,4-thiadiazolyl)methylthio)ethylamino]ethylene.

EXAMPLE 87

1-Nitro-2-methylamino-2-[2-((3-1,2,5-thiadiazolyl)methylthio)ethylamino]ethylene.

Reaction of 3-methyl-1,2,5-thiadiazole with N-bromosuccinimide results in the production of 3-bromomethyl-1,2,5-thiadiazole.

When 3-bromomethyl-1,2,5-thiadiazole is used as the starting material in the procedure of Example 42(ii) and 42(iii), the title compound is produced.

EXAMPLE 88

1-Nitro-2-methylamino-2-[2-(2-(2-amino-5-(1,3,4)-thiadiazolyl)ethylthio)ethylamino]ethylene 1-Amino-5-(1,3,4-thiadiazole)acetic acid is esterified with anhydrous ethanolic hydrogen chloride and the resulting ethyl ester is reduced with lithium aluminum hydride in tetrahydrofuran to give 2-amino-5-(2-hydroxyethyl)-1,3,4-thiadiazole. Treating this hydroxyethyl compound with thionyl chloride gives 2-amino-5-(2-chloroethyl)-1,3,4-thiadiazole.

Using 2-amino-5-(2-chloroethyl)-1,3,4-thiadiazole as the starting material in the procedure of Example 42(ii) and 42(iii) gives the title compound.

EXAMPLE 89

1-Nitro-2-methylamino-2-[3-(2-amino-5-(1,3,4-thiadiazolyl)thio)propylamino]ethylene Using 2-amino-5-(3-aminopropylthio)-1,3,4-thiadiazole (from the dihydrobromide) as the starting material in the procedure of Example 8(i) and (ii) gives the title compound.

EXAMPLE 90

1,1-Dicyano-2-[2-((2-amino-5-(1,3,4)-thiadiazolyl)methylthio)ethylamino]-2-[2-((4-methyl-5-imidazolyl)methylthio)ethylamino]ethylene By the procedure of Example 24(iii) reacting 2-amino-5-[(2-aminoethyl)thiomethyl]-1,3,4-thiadiazole with 1,1-dicyano-2-methylthio-2-[2-((4-methyl-5-imidazolyl)methylthio)ethylamino]ethylene, gives the title compound.

EXAMPLE 91

1-Cyano-2-[2-((2-amino-5-(1,3,4)-thiadiazolyl)methylthio)ethylamino]-2-[2-((4-methyl-5-imidazolyl)methylthio)ethylamino]ethylene.

By the same procedure as Example 25(ii) using as starting material 2-amino-5-[(2-aminoethyl)thiomethyl]-1,3,4-thiadiazole, the title compound is prepared.

EXAMPLE 92

Reaction of 2-amino-5-[(2-aminoethyl)thiomethyl]-1,3,4-thiadiazole by the procedure of Example 4 with the following compounds:
- 1-benzenesulphonyl-2-methylthio-2-[2-((4-methyl-5-imidazolyl)methylthio)ethylamino]ethylene,
- 1-(4-chlorobenzene)sulphonyl-2-methylthio-2-[2-((4-methyl-5-imidazolyl)methylthio)ethylamino]ethylene,
- 1-(3,4-dichlorobenzene)sulphonyl-2-methylthio-2-[2-((4-methyl-5-imidazolyl)methylthio)ethylamino]ethylene and
- 1-(4-methylbenzene)sulphonyl-2-methylthio-2-[2-((4-methyl-5-imidazolyl)methylthio)ethylamino]ethylene, results in the formation of the following products respectively:
- 1-benzenesulphonyl-2-[2-((2-amino-5-1,3,4-thiadiazolyl)methylthio)ethylamino]-2-[2-((4-methyl-5-imidazolyl)methylthio)ethylamino]ethylene,
- 1-(4-chlorobenzene)sulphonyl-2-[2-((2-amino-5-1,3,4-thiadiazolyl)methylthio)ethylamino]-2-[2-((4-methyl-5-imidazolyl)methylthio)ethylamino]ethylene,
- 1-(3,4-dichlorobenzene)sulphonyl-2-[2-((2-amino-5-1,3,4-thiadiazolyl)methylthio)ethylamino]-2-[2-((4-methyl-5-imidazolyl)methylthio)ethylamino]ethylene and
- 1-(4-methylbenzene)sulphonyl-2-[2-((2-amino-5-1,3,4-thiadiazolyl)methylthio)ethylamino]-2-[2-((4-methyl-5-imidazolyl)methylthio)ethylamino]ethylene.

EXAMPLE 93

1-Nitro-2-ethylamino-2-[2-((2-amino-5-1,3,4-thiadiazolyl)methylthio)ethylamino]ethylene Reaction of 1-nitro-2-methylthio-2-[2-((2-amino-5-(1,3,4)-thiadiazolyl)methylthio)ethylamino]ethylene (see Example 85(i)) with ethylamine by the procedure of Example 8(ii) gives the title product.

EXAMPLE 94

1-Nitro-2,2-bis-[2-((2-amino-5-1,3,4-thiadiazolyl)methylthio)ethylamino]ethylene When 2-amino-5-[(2-aminoethyl)thiomethyl]-1,3,4-thiadiazole is used as the starting material in the process of Example 67, the title compound is produced.

EXAMPLE 95

| Ingredients | Amounts |
| --- | --- |
| 1-Nitro-2-methylamino-2-[2-((2-amino-5-1,3,4-thiadiazolyl)methylthio)ethylamino]ethylene | 150 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE 96

| Ingredients | Amounts |
| --- | --- |
| 1-Nitro-2-methylamino-2-[3-((2-amino-5-1,3,4-thiadiazolyl)thio)propylamino]ethylene | 200 mg |
| Lactose | 100 mg |

The ingredients are mixed and filled into a hard gelatin capsule.

EXAMPLE 97

When, in the procedure of Example 14, the following compounds are reacted with 1,1-diphenylsulphonyl-2-methylthio-2-methylaminoethylene:
- 2-[3-aminopropylthio]oxazole,
- 3-[(2-aminoethyl)thiomethyl]isoxazole,
- 3-[(2-aminoethyl)thiomethyl]-1,2,4-triazole,
- 2-[2-aminoethyl)thiomethyl]thiazole,
- 3-[(2-aminoethyl)thiomethyl]isothiazole and
- 2-amino-5-[(2-aminoethyl)thiomethyl]-1,3,4-thiadiazole the products are:
- 1,1-diphenylsulphonyl-2-methylamino-2-[3-(2-oxazolylthio)propylamino]ethylene,
- 1,1-diphenylsulphonyl-2-methylamino-2-[2-(3-isoxazolylmethylthio)ethylamino]ethylene,
- 1,1-diphenylsulphonyl-2-methylamino-2-[2-(3-(1,2,4-triazolyl)methylthio)ethylamino]ethylene,
- 1,1-diphenylsulphonyl-2-methylamino-2-[2-thiazolylmethylthio)ethylamino]ethylene,
- 1,1-diphenylsulphonyl-2-methylamino-2-[2-(3-isothiazolylmethylthio)ethylamino]ethylene and
- 1,1-diphenylsulphonyl-2-methylamino-2-[2-((2-amino-5-1,3,4-thiadiazolyl)methylthio)ethylamino]ethylene.

By the same procedure, starting from:
- 1-cyano-1-nitro-2-methylthio-2-methylaminoethylene,
- 1-nitro-1-phenylsulphonyl-2-methylthio-2-methylaminoethylene and
- 1-cyano-1-phenylsulphonyl-2-methylthio-2-methylaminoethylene the corresponding products in which the 2-methylthio group has been displaced by a:
- 2-[3-(2-oxoazolylthio)propylamino],
- 2-[2-(3-isoxazolylmethylthio)ethylamino],
- 2-[2-(3-(1,2,4-triazolyl)methylthio)ethylamino],
- 2-[2-(2-thiazolylmethylthio)ethylamino],
- 2-[2-(3-isothiazolylmethylthio)ethylamino] or
- 2-[2-((2-amino-5-1,3,4-thiazolyl)methylthio)ethylamino]

group may be prepared.

EXAMPLE 98

1-Nitro-2-amino-2-[2-((4-methyl-5-imidazolyl)methyl-thio)ethylamino]ethylene

Reaction of 1-nitro-2-methylthio-2-[2-((4-methyl-5-imidazolyl)methylthio)ethylamino]ethylene (see Example 2(i)) with ammonia by the procedure of Example 2(ii) yields, after recrystallisation from methanol, the title compound, m.p. 193°–195° C.

EXAMPLE 99

1-Nitro-2,2-bis-[4-(5-bromo-4-imidazolyl)-butylamino]ethylene

Reaction of 5-bromo-4-(4-aminobutyl)imidazole with 1-nitro-2,2-bis-methylthioethylene in the procedure of Example 8(i) yields 1-nitro-2-methylthio-2-[4-(4-imidazolyl)butylamino]ethylene, m.p. 157°–158°, (from isopropanol).

(ii) When this methylthio compound is reacted with 5-bromo-4-(4-aminobutyl)imidazole in the procedure of Example 8(ii), the title compound is produced, m.p. 198°–199.5° (from ethanol).

EXAMPLE 100

1-Nitro-2-methylamino-2-[4-(5-bromo-4-imidazolyl)-butylamino]ethylene.

When 5-bromo-4-(4-aminobutyl)imidazole is reacted with 1-nitro-2,2-bis-methylthioethylene according to the procedure of Example 8(i) and the resultant 1-nitro-2-methylthio-2-[4-(5-bromo-4-imidazolyl)-butylamino]ethylene, m.p. 157°–158° treated with methylamine by the procedure of Example 8(ii), the title compound, m.p. 145°–148° is produced.

We claim:

1. A compound of the formula:

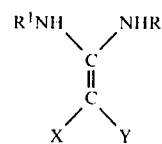

wherein X and Y, which may be the same or different, are hydrogen, nitro, cyano or $SO_2Ar$ but are not both hydrogen; $R^1$ is Het—$(CH_2)_mZ(CH_2)_n$; R is hydrogen, lower alkyl or Het—$(CH_2)_mZ(CH_2)_n$; Z is sulphur or methylene; m is 0, 1 or 2 and n is 2 or 3 provided that the sum of m and n is 3 or 4; Het is triazolyl which is attached at a ring carbon and is unsubstituted or substituted by lower alkyl, hydroxyl, halogen or amino; and Ar is phenyl unsubstituted or substituted by halogen or methyl or a pharmaceutically acceptable acid addition salt thereof.

2. A compound of claim 1 wherein X and Y are hydrogen, nitro or cyano, but are not both hydrogen; and R is hydrogen or lower alkyl.

3. A compound of claim 1 wherein R is methyl or Het-$CH_2SCH_2CH_2$: Z is sulphur; m is 1 and n is 2.

4. A compound of claim 1 wherein X is nitro and Y is hydrogen.

5. A pharmaceutical composition to inhibit H-2 histamine receptors comprising a pharmaceutical carrier and in an effective amount to inhibit said receptors a compound of claim 1.

6. A method of inhibiting H-2 histamine receptors which comprises administering to an animal in need thereof in an effective amount to inhibit said receptors a compound of claim 1.

* * * * *

UNITED STATES PATENT AND TRADEMARK OFFICE
CERTIFICATE OF CORRECTION

PATENT NO. : 4,317,829
DATED : March 2, 1982
INVENTOR(S) : Graham J. Durant, John C. Emmett, Charon R. Ganellin and Hunter D. Prain It is certified that error appears in the above—identified patent and that said Letters Patent is hereby corrected as shown below:

Column 4, lines 27-30, the first structural formula, XI, should appear as follows:

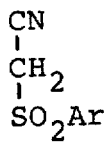

Column 4, lines 27-30, that part of SCHEME 4 reading $$\frac{1.\ \text{base}}{2.\ R^1NH}$$    should read    $$\frac{1.\ \text{base}}{2.\ R^1NH_2} \rightarrow$$

Signed and Sealed this

Thirty-first Day of August 1982

[SEAL]

Attest:

GERALD J. MOSSINGHOFF

Attesting Officer    Commissioner of Patents and Trademarks